United States Patent
Rubinfeld et al.

(10) Patent No.: US 10,092,594 B2
(45) Date of Patent: *Oct. 9, 2018

(54) COMPOSITIONS AND METHODS FOR TREATING OR PREVENTING DISEASES ASSOCIATED WITH OXIDATIVE STRESS

(71) Applicants: CXL Ophthalmics, LLC, Encinitas, CA (US); Brad Hartman, Renton, WA (US)

(72) Inventors: Roy S. Rubinfeld, Bethesda, MD (US); Raymond A. Hartman, Carlsbad, CA (US); Sandy T. Feldman, Del Mar, CA (US)

(73) Assignee: CXL Ophthalmics, LLC, Encinitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/335,146

(22) Filed: Oct. 26, 2016

(65) Prior Publication Data

US 2017/0071978 A1   Mar. 16, 2017

Related U.S. Application Data

(62) Division of application No. 14/387,803, filed as application No. PCT/US2013/034467 on Mar. 28, 2013, now Pat. No. 9,566,301.

(60) Provisional application No. 61/617,501, filed on Mar. 29, 2012.

(51) Int. Cl.
| | |
|---|---|
| A61K 33/18 | (2006.01) |
| A61K 9/08 | (2006.01) |
| A61K 9/00 | (2006.01) |
| A61K 38/44 | (2006.01) |
| A61L 26/00 | (2006.01) |
| A61K 31/525 | (2006.01) |

(52) U.S. Cl.
CPC ............ *A61K 33/18* (2013.01); *A61K 9/0014* (2013.01); *A61K 9/0048* (2013.01); *A61K 9/08* (2013.01); *A61K 31/525* (2013.01); *A61K 38/44* (2013.01); *A61L 26/0066* (2013.01); *C12Y 111/01006* (2013.01); *A61L 2300/106* (2013.01); *A61L 2300/254* (2013.01)

(58) Field of Classification Search
CPC .. A61K 31/525; A61K 33/18; A61K 2300/00; A61K 9/0048; A61K 9/08; A61N 5/062
See application file for complete search history.

(56) References Cited

U.S. PATENT DOCUMENTS

| | | |
|---|---|---|
| 3,132,068 A | 5/1964 | Sidney |
| 4,676,790 A | 6/1987 | Kern |
| 4,863,627 A | 9/1989 | Davies et al. |
| 5,368,590 A | 11/1994 | Itoh |
| 5,639,481 A | 6/1997 | Kessler et al. |
| 5,849,291 A | 12/1998 | Kessler et al. |
| 6,043,237 A | 3/2000 | Meadows et al. |
| 6,099,521 A | 8/2000 | Shadduck |
| 6,161,544 A | 12/2000 | Devore et al. |
| 6,162,210 A | 12/2000 | Shadduck |
| 6,183,086 B1 | 2/2001 | Neubert |
| 6,248,335 B1 | 6/2001 | Duan et al. |
| 6,309,656 B1 | 10/2001 | Pugliese et al. |
| 6,413,268 B1 | 7/2002 | Hartman |
| 6,447,537 B1 | 9/2002 | Hartman |
| 6,471,691 B1 | 10/2002 | Kobayashi et al. |
| 6,544,286 B1 | 4/2003 | Perez |
| 6,783,539 B1 | 8/2004 | Timberlake et al. |
| 6,880,558 B2 | 4/2005 | Perez |
| 7,015,252 B2 | 3/2006 | Fujii et al. |
| 7,044,945 B2 | 5/2006 | Sand |
| 7,073,510 B2 | 7/2006 | Redmond et al. |
| 7,077,839 B2 | 7/2006 | Hamblin et al. |
| 7,186,417 B1 * | 3/2007 | Siegel .................. A61K 9/0034 424/405 |
| 7,220,278 B2 | 5/2007 | Peyman |
| 7,288,106 B2 | 10/2007 | Heacock et al. |
| 7,331,350 B2 | 2/2008 | Kochevar et al. |
| 7,479,136 B2 | 1/2009 | Dotson |

(Continued)

FOREIGN PATENT DOCUMENTS

| | | |
|---|---|---|
| CA | 2319087 A1 | 8/1999 |
| CA | 2418306 A1 | 1/2002 |

(Continued)

OTHER PUBLICATIONS

Harvey et al (Toxicology in Vitro, 2010, vol. 24, pp. 1790-1796).*
Rieger (Graefe's Arch Clin Exp Ophthalmol, 2001, vol. 239, pp. 222-226).*
Iseli et al (Journal of Refractive Surgery, 2008, vol. 24, pp. S752-S755).*
International Search Report and Written Opinion for related international application No. PCT/US2013/033923, dated Jul. 12, 2013, in 13 pages.
International Search Report and Written Opinion PCT/US2011/033873 dated Jan. 17, 2012 in 14 pages.
International Search Report and Written Opinion for related international application No. PCT/US2013/034467 dated Jul. 26, 2013 in 12 pages.

(Continued)

*Primary Examiner* — Mark V Stevens
(74) *Attorney, Agent, or Firm* — Procopio, Cory, Hargreaves & Savitch LLP

(57) ABSTRACT

Methods and compositions for treating various indications by lessening oxidative stress in a patient are provided. A pharmaceutical composition comprises between about 0.001% to about 10.0%, or more specifically between about 0.015% to about 5%, sodium iodide or catalase by weight. The iodine ion or the catalase dissociates hydrogen peroxide into water and molecular oxygen to interrupt biological events that result in negative side effects. The pharmaceutical composition further comprises in some cases a reducing agent or various carrier materials. The pharmaceutical composition is in some cases formulated for a variety of delivery methods.

19 Claims, No Drawings

(56) References Cited

U.S. PATENT DOCUMENTS

| | | |
|---|---|---|
| 7,498,156 B2 | 3/2009 | Goodrich et al. |
| 7,727,544 B2 | 6/2010 | Schwartz et al. |
| 7,744,590 B2 | 6/2010 | Eells et al. |
| 7,753,943 B2 | 7/2010 | Strong |
| 7,943,590 B2 | 5/2011 | Flugelman |
| 8,034,373 B2 | 10/2011 | Reynolds et al. |
| 8,092,490 B2 | 1/2012 | Redmond et al. |
| 8,100,530 B2 | 1/2012 | Zhou et al. |
| 8,106,038 B2 | 1/2012 | Margaron et al. |
| 8,177,778 B2 | 5/2012 | Muller et al. |
| 8,215,314 B2 | 7/2012 | Chan et al. |
| 8,238,993 B2 | 8/2012 | Maynard et al. |
| 8,398,628 B2 | 3/2013 | Muller |
| 8,574,277 B2 | 11/2013 | Muller et al. |
| 8,580,789 B2 | 11/2013 | Krueger et al. |
| 9,125,856 B1 | 9/2015 | Paik et al. |
| 2001/0016731 A1 | 8/2001 | DeVore et al. |
| 2002/0006394 A1 | 1/2002 | Redmond et al. |
| 2002/0013577 A1 | 1/2002 | Frey et al. |
| 2002/0022606 A1 | 2/2002 | Kochevar et al. |
| 2003/0083649 A1 | 5/2003 | Margaron et al. |
| 2003/0105521 A1 | 6/2003 | Perez |
| 2003/0175259 A1 | 9/2003 | Karageozian et al. |
| 2003/0203839 A1* | 10/2003 | Kruzel .................. A61K 38/40 424/278.1 |
| 2003/0208190 A1 | 11/2003 | Roberts et al. |
| 2004/0137068 A1 | 7/2004 | Bhushan |
| 2005/0070942 A1 | 3/2005 | Perez |
| 2005/0124982 A1 | 6/2005 | Perez |
| 2005/0149006 A1 | 7/2005 | Peyman |
| 2005/0152993 A1 | 7/2005 | De Oliveira |
| 2005/0241653 A1 | 11/2005 | Van Heugten et al. |
| 2005/0271590 A1 | 12/2005 | Schwartz et al. |
| 2005/0283234 A1 | 12/2005 | Zhou et al. |
| 2006/0074487 A1 | 4/2006 | Gilg |
| 2006/0084951 A1 | 4/2006 | Heacock et al. |
| 2006/0134170 A1 | 6/2006 | Griffith et al. |
| 2006/0166879 A1 | 7/2006 | Bhushan et al. |
| 2006/0172972 A1 | 8/2006 | Bhushan et al. |
| 2006/0177430 A1 | 8/2006 | Bhushan et al. |
| 2006/0235513 A1 | 10/2006 | Price |
| 2006/0268231 A1 | 11/2006 | Gil et al. |
| 2006/0275278 A1 | 12/2006 | Choy et al. |
| 2007/0088415 A1 | 4/2007 | Peyman |
| 2007/0128174 A1 | 6/2007 | Kleinsek et al. |
| 2007/0129286 A1 | 6/2007 | Zhang |
| 2007/0135805 A1 | 6/2007 | Peyman |
| 2007/0142828 A1 | 6/2007 | Peyman |
| 2007/0167935 A1 | 7/2007 | Serdarevic |
| 2007/0207116 A1* | 9/2007 | Brown ................ A61K 31/717 424/78.3 |
| 2007/0225778 A1 | 9/2007 | Heacock et al. |
| 2008/0009901 A1 | 1/2008 | Redmond et al. |
| 2008/0015660 A1 | 1/2008 | Herekar |
| 2008/0039769 A1 | 2/2008 | Peyman |
| 2008/0057023 A1 | 3/2008 | Chynn |
| 2008/0097174 A1 | 4/2008 | Maynard et al. |
| 2008/0114283 A1 | 5/2008 | Mattson et al. |
| 2008/0139671 A1 | 6/2008 | Herekar |
| 2008/0161780 A1 | 7/2008 | Serdarevic |
| 2008/0208177 A1 | 8/2008 | Mrochen et al. |
| 2008/0246920 A1 | 10/2008 | Buczek et al. |
| 2008/0269119 A1 | 10/2008 | Griffith et al. |
| 2008/0269730 A1 | 10/2008 | Dotson |
| 2008/0288063 A1 | 11/2008 | Price, Jr. |
| 2009/0099557 A1 | 4/2009 | Sedarevic |
| 2009/0105127 A1 | 4/2009 | Thompson et al. |
| 2009/0149842 A1 | 6/2009 | Muller |
| 2009/0149923 A1 | 6/2009 | Herekar |
| 2009/0171305 A1 | 7/2009 | El Hage |
| 2009/0192437 A1 | 7/2009 | Soltz et al. |
| 2009/0275929 A1 | 11/2009 | Zickler |
| 2010/0057059 A1 | 3/2010 | Makino |
| 2010/0057060 A1 | 3/2010 | Herekar |
| 2010/0069894 A1 | 3/2010 | Mrochen et al. |
| 2010/0087920 A1 | 4/2010 | Marmo |
| 2010/0114109 A1 | 5/2010 | Peyman |
| 2010/0173019 A1 | 7/2010 | Paik et al. |
| 2010/0189817 A1 | 7/2010 | Krueger et al. |
| 2010/0210996 A1 | 8/2010 | Peyman |
| 2010/0286156 A1 | 11/2010 | Pinelli |
| 2010/0318017 A1 | 12/2010 | Lewis et al. |
| 2011/0060129 A1 | 3/2011 | Akashi et al. |
| 2011/0060267 A1 | 3/2011 | DeWoolfson et al. |
| 2011/0081323 A1 | 4/2011 | Kleinsek et al. |
| 2011/0086802 A1 | 4/2011 | Dewoolfson et al. |
| 2011/0118654 A1 | 5/2011 | Muller et al. |
| 2011/0125187 A1 | 5/2011 | Soltz et al. |
| 2011/0149247 A1 | 6/2011 | Artsyukhovich |
| 2011/0160710 A1 | 6/2011 | Frey et al. |
| 2011/0237999 A1 | 9/2011 | Muller et al. |
| 2011/0264082 A1 | 10/2011 | Mrochen et al. |
| 2011/0282333 A1 | 11/2011 | Herekar et al. |
| 2011/0288466 A1 | 11/2011 | Muller et al. |
| 2011/0301524 A1 | 12/2011 | Bueler et al. |
| 2011/0306956 A1 | 12/2011 | Islam |
| 2012/0059439 A1 | 3/2012 | Yoon |
| 2012/0065572 A1 | 3/2012 | Lewis et al. |
| 2012/0083772 A1 | 4/2012 | Rubinfeld et al. |
| 2012/0095455 A1 | 4/2012 | Rodmond et al. |
| 2012/0121567 A1 | 5/2012 | Troisi et al. |
| 2012/0203161 A1 | 8/2012 | Herekar |
| 2012/0215155 A1 | 8/2012 | Muller et al. |
| 2012/0238938 A1 | 9/2012 | Herekar et al. |
| 2012/0283531 A1 | 11/2012 | Maynard et al. |
| 2012/0283621 A1 | 11/2012 | Muller |
| 2012/0289886 A1 | 11/2012 | Muller et al. |
| 2012/0310083 A1 | 12/2012 | Friedman et al. |
| 2012/0310141 A1 | 12/2012 | Kornfield et al. |
| 2013/0060187 A1 | 3/2013 | Friedman et al. |
| 2013/0079759 A1 | 3/2013 | Dotson et al. |
| 2013/0085370 A1 | 4/2013 | Friedman et al. |
| 2013/0158342 A1 | 6/2013 | Chan et al. |
| 2013/0245536 A1 | 9/2013 | Friedman et al. |
| 2015/0032686 A1 | 1/2015 | Kuchoor |
| 2015/0126921 A1 | 5/2015 | Rubinfeld et al. |

FOREIGN PATENT DOCUMENTS

| | | | |
|---|---|---|---|
| CA | 2473703 A1 | 7/2003 | |
| CA | 2511217 A1 | 7/2004 | |
| CA | 2515720 A1 | 9/2004 | |
| CA | 2566961 A1 | 12/2005 | |
| CA | 2576308 A1 | 2/2006 | |
| CA | 2577025 A1 | 2/2006 | |
| CA | 2700884 A1 | 2/2009 | |
| JP | 54101440 A | 8/1979 | |
| RU | 1803110 A1 | 3/1993 | |
| WO | 2001082933 A2 | 11/2001 | |
| WO | WO 0211716 A2 * | 2/2002 | ........... A61K 9/0095 |
| WO | 2003061518 A2 | 7/2003 | |
| WO | 2003068247 A1 | 8/2003 | |
| WO | 2004024035 A1 | 3/2004 | |
| WO | 2005117987 A1 | 12/2005 | |
| WO | 2007011874 A2 | 1/2007 | |
| WO | 2007011875 A2 | 1/2007 | |
| WO | 2007020673 A1 | 2/2007 | |
| WO | 2007026382 A1 | 3/2007 | |
| WO | 2007035843 A2 | 3/2007 | |
| WO | 2007082127 A2 | 7/2007 | |
| WO | 200805059 A2 | 1/2008 | |
| WO | 2008055118 A2 | 5/2008 | |
| WO | 2009001396 A2 | 12/2008 | |
| WO | 2009146151 A2 | 12/2009 | |
| WO | 2010023705 A1 | 3/2010 | |
| WO | 2010093908 A2 | 8/2010 | |
| WO | 2011011202 A1 | 1/2011 | |
| WO | 2011019940 A2 | 2/2011 | |
| WO | 2011041437 A1 | 4/2011 | |
| WO | 2011050164 A1 | 4/2011 | |
| WO | 2011056477 A2 | 5/2011 | |
| WO | 2011109712 A2 | 9/2011 | |
| WO | 2011152861 A2 | 12/2011 | |

(56) References Cited

FOREIGN PATENT DOCUMENTS

| WO | 2012035403 A1 | 3/2012 |
| WO | 2012047307 A1 | 4/2012 |
| WO | 2013148896 A1 | 10/2013 |

OTHER PUBLICATIONS

Agbor, et al. "Effect of Iodine Supplementation on Antioxidant Status of Normal and Alloxan Monohydrate in Toxicated Rats", International Journal of Pharmacology, 7 (6): pp. 726-731, 2011, Asian Network for Scientific Information.
Baert et al (Medical Radiology: Diagnostic Imaging, Radiological Imaging of the Ureter, copyright 2003, Springer).
ABRAXIS (Iodopen MSDS, Revision date of Jun. 13, 2006).
Partial supplementary European Search Report for EP 13768403.1 dated Oct. 23, 2015 in 10 pages.
Horwath-Winter J, et al: "Iodide iontophoresis as a treatment for dry eye syndrome", The British Journal of Ophthalmology, Jan. 2005, pp. 40-44, vol. 89, No. 1.
Singh et al: "Clinical Evaluation of Sodium Iodide in the Treatement of Various Types of Cataracts", Journal of the Indian Medical Association, 1983, pp. 119-121, vol. 81, No. 7-8.
Winkler et al: "Effect of Iodide on Total Antioxidant Status of Human Serum", Cell Biochemistry and Function, Jun. 2000, pp. 143-146, vol. 18, No. 2.
Ilens Ophthalmic Solution, http://naikutty.in/medicine-list-i/article/86937-ilens-solution, Date unknown but available prior to the date of this application.
Wollensak et al., "Cross-linking of scleral collagen in the rabbit using riboflavin and UVA", ACTA Ophthalmologica Scandinavica, 2005, vol. 83, pp. 477-482.
International Search Report and Written Opinion for related international application No. PCT/US2013/034185, dated Jul. 11, 2013, in 12 pages.
International Preliminary Report on Patentability for PCT/US2013/034185, dated Oct. 1, 2014, in 7 pages.
Wollensak et al. "Corneal Endothelial Cytotoxicity of Riboflavinf/UVA Treatment in vitro." Ophthalmic Res. 35:324-328, 2003.
Wollensak et al. "Endothelial cell damage after riboflavin-ultraviolet-A treatment in the rabbit." J Cataract Refract Surg. 29:1786-1790, 2003.
Wollensak et al. "Keratocyte Apoptosis After Corneal Collagen Cross-linking Using Riboflavin/UVA Treatment." Cornea. 23(1):43-49, Jan. 2004.
Wollensak et al. "Keratocyte cytotoxicity of riboflavin/UVA treatment in vitro." Eye. 2004, in 5 pages.
EMX Industries, Inc.; ColorMax HEX Color Sensors; Mar. 2010.
Wells et al. "Oxidative Stress in Developmental Origins of Disease: Teratogenesis, Neurodevelopmental Deficits, and Cancer." Toxicological Sciences. 108(1):4-18 (2009).
Uttara et al. "Oxidative Stress and Neurodegenerative Diseases: A Review of Upstream and Downstream Antioxidant Therapeutic Options." Current Neuropharmacology. 7:65-74 (2009).
Sukkar et al. "Oxidative stress and nutritional prevention in autoimmune rheumatic diseases." Autoimmunity Reviews. 3:199-206 (2004).
Bickers et al. "Oxidative Stress in the Pathogenesis of Skin Disease." The Society for Investigative Dermatology. pp. 2565-2575, 2006.
"Gilgun-Sherki et al. ""Oxidative stress induced-neurodegenerative diseases: the need forantioxidants that penetrate the blood brain barrier."" Neuropharmacology. 40:959-975 (2001)."
Oduntan et al. "A review of the role of oxidative stress in the pathogenesis of eye diseases." S Afr Optom. 70(4):191-199 (2011).
Kato et al. "Topography-Guided Conductive Keratoplasty: Treatment for Advanced Keratoconus." American Journal of Ophthalmology. 150(4):481-489 (Oct. 2010).
Kohnen et al. "Bewertung und Qualitätssicherung refraktivchirurgischer Eingriffe durch die DOG und den BVA (Evaluation and quality assurance of refractive surgery by the German Ophthalmological Society and the Professional Association of German Ophthalmologists)." Ophthalmologie. 108(9):869-882 (Sep. 2011). English Abstract provided on p. 871.
Wollensak et al. "Long-term biomechanical properties of rabbis cornea after photodynamic collagen crosslinking." Acta Ophthalmologica. 87:48-51, 2009.
Kullman. "Alternative Applications of the Femtosecond Laser in Ophthalmology." Seminars in Ophthalmology. 25 (5-6):256-264 (Nov. 2010).
Chuo et al. "Modem Corneal and Refractive Procedures." Expert Review of Ophthalmology. 6(2):247-266 (Apr. 2011).
Epstein."Refraktive Chirurgie." Therapeutische Umschau. Revue Therapeutique. 66(3):207-210 (Mar. 2009). English abstract.
Wollensak et al. "Riboflavin/Ultraviolet-A-induced Collagen Crosslinking for the Treatment of Keratoconus." Am J Ophthalmol. 135:620-627, 2003.
Wollensak et al. "Wound Healing in the Rabbit Cornea After Corneal Collagen Cross-Linking With Riboflavin and UVA." Cornea. 26:600-605, 2007.
Wollensak et al. "Stress-strain measurements of human and porcine corneas after riboflavin-ultraviolet-A-induced cross-linking." J Cataract Refract Surg. 29:1780-1785, 2003.
Elstner et al. "Uptake and Biochemical Activity of Potassium Iodide in Isolated Rabbit Eyes." XP008167001. Ophtlalmologica. 191(2):122-126 (1985). English abstract provided.
El-Raggal, "Riboflavin-Ultraviolet a Corneal Cross linking for Keratoconus", Middle East African Journal of Opthalmology, Oct.-Dec. 2009; 16(4): 256-259, 8 pages.
Supplementary European Search Report for EP 13767439.6 dated Sep. 15, 2015 in 6 page.
Rose, R. C. et al.: "Ocular oxidants and antioxidant protection", Experimental Biology and Medicine, vol. 217, No. 4, 1998, pp. 397-407.
Ibusuki et al.: "Photochemically Cross-Linked Collagen Gels as Three-Dimensional Scaffolds for Tissue Engineering", Tissue Engineering, vol. 13, No. 8, Aug. 14, 2007, pp. 1995-2001.
Rieger, "Anti-oxidative Capacity of Various Artificial Tear Preparations", Graefe's Arch. Clin. Exp. Opthalmol., 2001, vol. 239, pp. 222-226.
Wollensak et al. "Collagen Fiber Diameter in the Rabbit Cornea After Collagen Crosslinking by Riboflavin/UVA." Cornea. 23(5):503-507, Jul. 2004.
Bessonova et al. "A study of the stability of eye drops containing riboflavine (Russian)." XP002719481. Database accession No. EMB-1978057912. Abstract. Database EMBASE (Online). Elsevier Science Publishers, Amsterdam, NL, 1977.
Koltun et al. "Improving the production technology of vitamin-containing eye drops to ensure their microbiological purity." XP002719482. Database accession No. PREV199497454025. Abstract. Database BIOSIS (Online). Biosciences Information Service, Philadelphia, PA, US, 1993.
Rieger, et al. "The Effect of Iodide Iontophoresis on the Antioxidative Capacity of the Tear Fluid" Graefe's Archive for Clinical Experimental Ophthalmology. 248:1639-1646 (2010).
Schmut et al. "Iodide protection from UVB irradiation-induced degradation of hyaluronate and against UVB-damage pf human conjunctival fibroblasts." XP008166988. Graefe's Archive for Clinical Experimental Ophthalmology. 242 (4):279-283 (2004).
Shimmura et al. "Subthreshold UV Radiation-induced Peroxide Formation in Cultured Corneal Epithelial Cells: The Protective Effects of Lactoferrin." XP055098621. Experimental Eye Research. 63(5):519-526 (1996).
Ishimitsu et al. "The photochemical decomposition and hydroxylation of phenylalanine in the presence of riboflavin." XP008167014. Chemical and Pharmaceutical Bulletin, Pharmaceutical Society of Japan. 33(4):1552-1556 (1985).
Zhang et al. "Clinical effect of traditional Chinese herb combined with sodium iodide in treating corneal opacity." XP002719483. Database accession No. EMB-2007125131. Database EMBASE (Online). Elsevier Science Publishers, Amsterdam, NL, Feb. 2007.
Extended European Search Report dated Feb. 10, 2014 for related EP Patent Application No. 11831060 in 15 pages.

(56) References Cited

OTHER PUBLICATIONS

Cho et al. "Reactive Oxygen Species-Induced Apoptosis and Necrosis in Bovine Corneal Endothelial Cells." Investigative Ophthalmology & Visual Science. 40(5):911-919, Apr. 1999.

Fujimori. "Cross-linking and fluorescence changes of collagen by glycation and oxidation." Biochimica et Biophysica Acta. 998:105-110, 1989.

Hull et al. "Hydrogen Peroxide-Mediated Corneal Endothelial Damage." Investigative Ophthalmology & Visual Science. 25:1246-1253, 1984.

Iseli et al. "Efficacy and Safety of Blue-light Scleral Cross-linking." International Congress of Corneal Cross-Linking, Dec. 7-8, 2007; Zurich, Switzerland. pp. S752-S755.

Khadem et al. "Photodynamic Biologic Tissue Glue." Cornea. 13(5):406-410, 1994.

Kohlhaas et al. "Biomechanical evidence of the distribution of cross-links in corneas treated with riboflavin and ultraviolet A light." J Cataract Refract Surg. 32:279-283, Feb. 2006.

Krueger et al. "Rapid vs Standard Collagen CXL with Equivalent Energy Dosing." Third International Congress of Corneal Crosslinking. Dec. 7-8, 2007; Zurich, Switzerland, in 25 pages.

Sato et al. "The Primary Cytotoxicity in Ultraviolet-A-Irradiated Riboflavin Solution is Derived from Hydrogen Peroxide." the Society for Investigative Dermatology, Inc. 105(4):608-612, Oct. 1995.

Seiler et al. "Corneal Cross-Linking-Induced Stromal Demarcation Line." Clinical Science. 25(9):1057-1059, Oct. 2006.

Spoerl et al. "Increased resistance of crosslinked cornea against enzymatic digestion." Current Eye Research. 29 (1):35-40, 2004.

Spoerl et al. "Induction of Cross-links in Corneal Tissue." Exp. Eye Res. 66:97-103, 1998.

Spoerl et al. "Safety of UVA-Riboflavin Cross-Linking of the Cornea." Cornea. 26(4):385-389, May 2007.

Spoerl et al. "Thermomechanical Behavior of Collagen-Cross-Linked Porcine Cornea." Ophthalmologica. 218:136-140, 2004.

\* cited by examiner

COMPOSITIONS AND METHODS FOR TREATING OR PREVENTING DISEASES ASSOCIATED WITH OXIDATIVE STRESS

CROSS-REFERENCE

This application is a divisional of application Ser. No. 14/387,803 filed on Sep. 24, 2014, which is a 371 of PCT/US2013/034467 filed on Mar. 28, 2013, which claims priority to U.S. Provisional Application No. 61/617,501, filed Mar. 29, 2012, and the contents of each of the foregoing applications are incorporated herein by reference in their entirety.

BACKGROUND

Collagen cross-linking is a parasurgical treatment for multiple ophthalmic disorders. In some cases, collagen cross-linking may also be combined with other treatments to improve corneal strength or optical refraction. Treatment methods include mini asymmetric radial keratotomy, corneal ring segment inserts, or topography-guided laser. Corrective lenses are normally required after these treatments, but with smaller, more normalized prescriptions. Increased corneal symmetry allows for more comfortable contact lens wear, often of daily disposable lenses. Collagen crosslinking limits deterioration of vision, increases unaided and uncorrected vision, and may reduce the need for corneal transplantation.

SUMMARY

Disclosed herein, in certain embodiments, is a pharmaceutical composition for treating oxidative stress in an individual in need thereof, comprising (a) 0.001% to 10.0% sodium iodine or catalase by weight, and (b) a pharmaceutically-acceptable excipient. In some embodiments, the pharmaceutical composition comprises about 0.015% to about 5% sodium iodine or catalase by weight. In some embodiments, the pharmaceutical composition comprises about 0.001%, about 0.01%, about 0.1%, about 1%, about 2%, about 3%, about 4%, about 5%, about 6%, about 7%, about 8%, about 9%, or about 10% sodium iodide or catalase by weight. In some embodiments, the composition has a basic pH. In some embodiments, the basic pH is between 7 and 8.4. In some embodiments, the pharmaceutical composition further comprises a reducing agent. In some embodiments, the reducing agent is thiosulfate, vitamin C, or sodium bisulfate. In some embodiments, the pharmaceutically-acceptable excipient is a thickener, an oil phase, a surfactant, a preservative, or a pH adjusting agent. In some embodiments, the pharmaceutical composition is a solution, emulsion, cream, ointment, lotion, gel, powder, solid, tincture, paste, vapor, tape, or lotion.

Disclosed herein, in certain embodiments, is a method of treating a disease, disorder or condition characterized by unwanted or excessive oxidative stress in an individual in need thereof, comprising administering to the individual a pharmaceutical composition comprising about 0.001% to about 10.0% sodium iodine or catalase by weight. In some embodiments, the pharmaceutical composition comprises about 0.015% to about 5% sodium iodine or catalase by weight. In some embodiments, the pharmaceutical composition comprises about 0.001%, about 0.01%, about 0.1%, about 1%, about 2%, about 3%, about 4%, about 5%, about 6%, about 7%, about 8%, about 9%, or about 10% sodium iodide or catalase by weight. In some embodiments, the composition has a basic pH. In some embodiments, the basic pH is between 7 and 8.4. In some embodiments, the pharmaceutical composition further comprises a reducing agent. In some embodiments, the reducing agent comprises thiosulfate, vitamin C, or sodium bisulfate.

In some embodiments, the disease, disorder or condition is ectasia. In some embodiments, the disease, disorder or condition is Glaucoma; Dry Eyes; Degenerative Retinal Damage (ARMD); Cataractogenesis; Retinopathy of Prematurity (ROP); Ocular Uveitis; or Cataracts. In some embodiments, the disease, disorder or condition is Burns, Dermatitis; Psoriasis; Vitiligo, Androgenic Alopecia; or Onset of Gray Hair.

In some embodiments, the disease, disorder or condition is arthritis. In some embodiments, the disease, disorder or condition is Keshan Disease; Myocardial Infarction; Atherosclerosis; Arterial Sclerosis. In some embodiments, the disease, disorder or condition is Asthma; Acute Respiratory Distress Syndrome (ARDS); Hyperoxia and Pulmonary Edema. In some embodiments, the disease, disorder or condition is Inflammatory Bowel Disease (IBD); Crohn's Disease; Ischemic Bowel Disease; Cancer; Inflammatory Immune Response; Diabetes; Injury Ischemia Reflow Injury; Vasospasm; Hemolytic Anemia; Progeria and Progressive Systemic Sclerosis. In some embodiments, the disease, disorder or condition is Hepatic Cirrhosis; Renal Graft; Glomerulonephritis and Endotoxin Liver Injury. In some embodiments, the disease, disorder or condition is Parkinson's Disease; Alzheimer's Disease; Schizophrenia; Cerebral Edema; Cerebral Infarction; Epilepsy; Bipolar Disorder. In some embodiments, the disease, disorder or condition is Wrinkling; Baldness; Presbyopia; Cataracts; Hearing loss; Hypertension; Memory loss.

Disclosed herein, in certain embodiments, is a method of healing a wound, comprising contacting the wound with a pharmaceutical composition comprising about 0.001% to about 10.0% sodium iodine or catalase by weight. In some embodiments, the pharmaceutical composition comprises between about 0.015% to about 5% sodium iodine or catalase by weight. In some embodiments, the pharmaceutical composition comprises about 0.001%, about 0.01%, about 0.1%, about 1%, about 2%, about 3%, about 4%, about 5%, about 6%, about 7%, about 8%, about 9%, or about 10% sodium iodide or catalase by weight. In some embodiments, the composition has a basic pH. In some embodiments, the basic pH is between 7 and 8.4. In some embodiments, the pharmaceutical composition further comprises a reducing agent. In some embodiments, the reducing agent comprises thiosulfate, vitamin C, or sodium bisulfate. In some embodiments, the wound is associated with refractive corneal surgery, thermokeratoplasty treatment, lens-based refractive surgery, retinal surgery, scleral surgery, retinal or glaucoma laser surgery, cataract and eye lid surgery, heart surgery. In some embodiments, the corneal surgery is PRK, LASIK, Intacs, lamellar corneal procedures, CK, or any combinations thereof. In some embodiments, the heart surgery is angioplasty.

Disclosed herein, in certain embodiments, is a method of reducing or preventing oxidative stress in a tissue undergoing photochemical crosslinking, comprising contacting the tissue with a pharmaceutical composition comprising between about 0.001% to about 10.0% sodium iodine or catalase by weight. In some embodiments, the pharmaceutical composition comprises between about 0.015% to about 5% sodium iodine or catalase by weight. In some embodiments, the pharmaceutical composition comprises about 0.001%, about 0.01%, about 0.1%, about 1%, about 2%, about 3%, about 4%, about 5%, about 6%, about 7%, about 8%, about 9%, or about 10% sodium iodide or catalase by weight. In some embodiments, the composition has a basic pH. In some embodiments, the basic pH is between 7 and 8.4. In some embodiments, the pharmaceutical composition further comprises a reducing agent. In some embodiments, the reducing agent comprises thiosulfate, vitamin C, or sodium bisulfate.

Disclosed herein, in certain embodiments, are compositions for reducing oxidative stress, comprising iodide ion and a pharmaceutically-acceptable excipient. In some embodiments, the composition is safe. In some embodiments, the composition lessens oxidative stress in vivo. In some embodiments, the composition comprises sodium iodide (NaI). In some embodiments, the composition comprises between about 0.001% to about 10.0% sodium iodide by weight. In specific embodiments, the composition comprises between about 0.015% to about 5% sodium iodide by weight. In some embodiments, the iodide ion is kept in the ionized form by maintaining the composition at a basic pH. In some specific embodiments the pH of the composition is between about 7.0 and about 8.4. Included in the embodiments described herein are all combinations and subcombinations of ranges and specific integers encompassed therein.

Other features and advantages of the present disclosure will become more readily apparent to those of ordinary skill in the art after reviewing the following detailed description and accompanying drawings.

DETAILED DESCRIPTION OF ILLUSTRATIVE EMBODIMENTS

After reading this description it will become apparent to one skilled in the art how to implement the compositions and methods of the present disclosure in various alternative embodiments and alternative applications. However, although various embodiments of the present disclosure will be described herein, it is understood that these embodiments are presented by way of example only, and not limiting. As such, this detailed description of various alternative embodiments should not be construed to limit the scope or breadth of the present disclosure as set forth in the appended claims.

Cells obtain energy from the oxidation of a variety of organic molecules, and oxygen is the primary oxidant in the biochemical reactions that perform this function. Oxidative stress represents an imbalance between the production and manifestation of reactive oxygen species and a biological system's ability to readily detoxify the reactive intermediates or to repair the resulting damage.

In humans, oxidative stress contributes to diseases ranging from Alzheimer's, heart disease and stroke to macular degeneration (the leading cause of adult blindness), dry eye, glaucoma and cancer. However, increased oxidative stress also causes an adaptive reaction which produces increased stress resistance and a long-term reduction of oxidative stress (in a process names mitohormesis). Mitohormesis is associated with the anti-aging effects of glucose restriction and physical exercise.

The compositions of the present disclosure comprise catalase and/or iodide ion, decrease oxidative stress in vivo and exhibit a beneficial or salutary effect on many diseases and health maintenance.

The anti-oxidative compositions described herein are capable of treating, reversing or partially reversing, or preventing diseases associated with oxidative stress due to active oxygen species, free radicals, or the like, in vivo, thereby preventing the occurrence or worsening of a disease or condition.

Exemplary Terms

As used herein, the terms "comprising," "including," and "such as" are used in their open, non-limiting sense.

The term "about" is used synonymously with the term "approximately." Illustratively, the use of the term "about" indicates that values slightly outside the cited values, i.e., plus or minus 0.1% to 10%, which are also effective and safe.

"Antioxidants" include, e.g., butylated hydroxytoluene (BHT), butylated hydroxyanisole (BHA), sodium ascorbate, and tocopherol.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone®, CL, Kollidon® CL, Polyplasdone® XL-10), larch arabogalactan, Veegum®, polyethylene glycol, waxes, sodium alginate, and the like.

"Bioavailability" refers to the extent to which an active moiety, e.g., drug, prodrug, or metabolite, is absorbed into the general circulation and becomes available at the site of drug action in the body. Thus, a compound administered through IV is 100% bioavailable. "Oral bioavailability" refers to the extent to with the compound is absorbed into the general circulation and becomes available at the site of the drug action in the body when a compound is taken orally.

"Carrier materials" include any commonly used excipients in pharmaceutics and should be selected on the basis of compatibility with the active ingredient and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott William & Wilkins 1999).

"Oxidative stress" refers to the condition characterized by an excess of oxidants and/or a decrease in antioxidant levels. Cellular oxidants include, but are not limited to, one or more of: radicals of oxygen (superoxide anion, hydroxyl radical, and/or peroxy radicals); reactive non-radical oxygen species such as, for example, hydrogen peroxide and singlet oxygen; carbon radicals; nitrogen radicals; and sulfur radicals. The condition of oxidative stress results in, for example, cellular damage, inflammation, impaired performance of cells and/or cell death.

"Prevent" or "prevention" means no disorder or disease development if none had occurred, or no further disorder or disease development if there had already been development. Also considered is the ability of one to prevent or reduce some or all of the symptoms associated with the disorder or disease.

"Surfactants" include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF); and the like.

A "therapeutically effective amount" or "effective amount" is that amount of a compound, material, composition, and/or dosage form as described herein that is in at least some cases effective to achieve a particular biological result. Such results in at least some cases include, but are not limited to, reduction and/or prevention of oxidative stress. Such effective activity is achieved in at least some cases, for example, by causing the ingestion of compositions according to aspects of the present disclosure. The term "therapeutically effective amount" includes, for example, a prophylactically effective amount. An "effective amount" is an amount effective to achieve a desired pharmacologic effect or therapeutic improvement without undue adverse side effects. The effective amount of a pharmaceutical agent will be selected by those skilled in the art depending on the particular patient and the disease level. It is understood that "an effective amount" or "a therapeutically effective amount" varies in at least some cases from subject to subject, due to variation in metabolism of therapeutic agents, age, weight, general condition of the subject, the condition being treated, the severity of the condition being treated, and the judgment of the prescribing physician.

"Treat" or "treatment" includes preventing a disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression (or partial regression) of the disorder or disease, relieving a condition caused by the disease or disorder, stopping the symptoms of the disease or disorder, or reversing or partially reversing certain diseases and/or conditions. Thus, as used herein, the term "treat" is used synonymously with the term "prevent."

Oxidative Stress Cycle

Oxidative stress processes often have a self-regenerating nature. For example, oxidative stress leads to further oxidative stress and the cycle reinforces itself. By way of example only, moderate $H_2O_2$ or $OH^-$ disrupts the mitochondria of cells causing an increase of superoxide anion production. Disruption of mitochondria leads to increased hydrogen peroxide production and the effect becomes exponentially self-regenerating. This often results in a severe disorder. Disruption of an oxidative stress cycle allows natural mechanisms to address the source of the initial oxidative stress.

In certain instances, increased or undesired peroxide levels in a tissue (for example, ocular tissue) results from the inactivation (in a reversible reaction) of endogenous catalase by nitric oxide. Catalase activity is affected by the presence of nitric oxide which binds to the active center of catalase. When the nitric oxide molecule is present the catalase is unable to attach itself to a peroxide molecule. As the partial pressure of nitric oxide gas in the tissue drops, the nitric oxide dissociates from the catalase and the catalase becomes active again. Thus nitric oxide is a reversible inhibitor of catalase.

Inactivation of catalase results in the build-up of peroxide which results in damage to a tissue and an inflammatory response. As the inflammatory response increases, more nitric oxide is produced rendering more catalase inactive and increasing the concentration of peroxide. Because nitric oxide prevents the catalase from working, adding additional catalase often does not fully inhibit or sufficiently reduce peroxide build-up. In some embodiments, iodide ion inhibits the build-up of peroxide because the iodide ion is not subject to inactivation by nitric oxide.

There are a number of agents that inactivate catalase, and result in the build-up of the oxidative cycle and cell death. For example, many chemotherapeutic agents are designed to activate or increase the oxidative cycle. Calcitriol, a catalase inhibitor, is used to kill cancer cells by peroxide build up.

Pharmaceutical Compositions

Disclosed herein, in certain embodiments, are compositions for reducing oxidative stress, comprising iodide ion and a pharmaceutically-acceptable excipient. In some embodiments, the composition comprises sodium iodide (NaI), catalase or a combination thereof. In some embodiments, the composition comprises between about 0.001% to about 10.0% sodium iodide by weight. In specific embodiments, the composition comprises between about 0.015% to about 5% sodium iodide by weight. In some embodiments, the iodide ion is kept in the ionized form by maintaining the composition at a basic pH. In some specific embodiments the pH of the composition is between about 7.0 and about 8.4. In some embodiments, the composition is safe. In some embodiments, the composition lessens oxidative stress in vivo. Included in the embodiments described herein are all combinations and subcombinations of ranges and specific integers encompassed therein.

In some embodiments, the compositions disclosed herein react as follows:

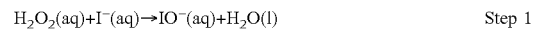

Step 1

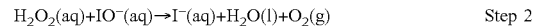

Step 2

These equations describe the reaction that occurs between iodide ion and hydrogen peroxide in basic solutions (pH of 7.0 or higher). The net result of the above equations is:

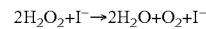

This illustrates the iodide ion is just a catalyst and is unchanged during the reaction. Iodide ion is a catalyst to break hydrogen peroxide into water and oxygen in non-acidic solutions, but in acidic solutions the following reaction occurs:

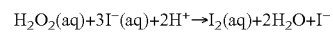

In oxidizing acid solutions the reaction of iodide ion and peroxide (referred to in the chemical literature as the Iodide ClockReaction) will precipitate elemental iodide out of solution.

In some embodiments of the pharmaceutical compositions described herein, a reducing agent is included. Non-limiting examples of reducing agents include sodium thiosulfate, vitamin C or sodium bisulfate.

Below is an example of the reaction of iodide with the thiosulfate:

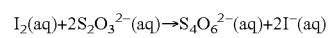

An advantage of an iodide ion as a peroxide reducing agent in inflamed tissue is that it is not persistent in the tissue. Once the peroxide cycle has been broken and inflammation subsides the NO pressure drops and the native catalase keeps the peroxide at a normal basal level. In some embodiments, other enzymes also begin to work once the peroxide levels drop.

The compositions described herein are administered and dosed in accordance with good medical practice, taking into account the clinical condition of the individual patient, the site and method of administration, scheduling of administration, and other factors known to medical practitioners. In human therapy, it is important in many cases to provide a dosage form that delivers the required therapeutic amount of the drug in vivo, and renders the drug bioavailable in a timely manner.

Treatment dosages generally are titrated to optimize safety and efficacy. Typically, dosage-effect relationships from in vitro and/or in vivo tests initially provide useful guidance on the proper doses for subject administration. Studies in animal models generally are used for guidance regarding effective dosages for treatment of the conditions, disorders or diseases in accordance with the present disclosure. In terms of treatment protocols, it should be appreciated that the dosage to be administered will depend on several factors, including the particular agent that is administered, the route chosen for administration, the age of the subject, and the condition of the particular subject.

In some embodiments, unit dosage forms of the pharmaceutical compositions disclosed herein comprise between about 0.001% to 10.0% sodium iodide by weight. In specific embodiments, the pharmaceutical compositions comprise between about 0.015% to about 5% sodium iodide by weight. In some embodiments, the pharmaceutical compositions comprise about 0.001%, about 0.01%, about 0.1%, about 1%, about 2%, about 3%, about 4%, about 5%, about 6%, about 7%, about 8%, about 9%, or about 10% sodium iodide by weight. Included in these embodiments are all combinations and subcombinations of ranges and specific integers encompassed therein.

Generally speaking, one will desire a pharmaceutical composition that provides an amount of an iodide ion that is effective to achieve the therapeutic effect desired when administered to a subject. Determination of these parameters is well within the skill of the art. These considerations are well known in the art and are described in standard textbooks.

Photochemical Crosslinking Compositions

Described herein are compositions for photochemical crosslinking comprising (1) riboflavin, and (2) an iodide ion and/or catalase. In some embodiments, the compositions are saturated with oxygen. In some embodiments, the compositions comprise a higher oxygen content than existing compositions. In some embodiments, the compositions further comprise artificial tear solutions, for example to keep the eye hydrated during the procedure or to reoxygenate the eye during the procedure. In some embodiments, the compositions further comprise a high lipid solution (or other ingredient) for reoxygenation. In some embodiments, the iodide ion and/or catalase enzyme serve to decompose hydrogen peroxide into water and molecular oxygen.

Iodide ions are small and mobile and exhibit little difficulty getting into the corneal stroma where the crosslinking takes place. Iodide ions also exhibit rapid diffusion and lack of post-procedural persistence. Catalase is a large enzyme and as a result it is difficult for the catalase to penetrate into the corneal stroma where the crosslinking takes place. When a catalase enzyme is used, steps must be taken early in the crosslinking procedure to disrupt the barrier functions of the corneal epithelium for riboflavin infusion. This reduced barrier function also allows easy introduction of the iodide ion. Non-limiting examples of epithelial barrier disruption include mechanical treatments and the use of chemicals such as benzylalkonium chloride.

Catalase enzyme is excellent for the decomposition of the peroxide in the following ways; it's naturally found in tissue and cells, it's not pH sensitive, and it doesn't quench the photochemical reaction between riboflavin and UV/blue light. Catalase enzyme works well in photochemical crosslinking compositions disclosed herein to protect the viability of the riboflavin against oxidation during storage and transport, and work well on the corneal epithelium to protect the epithelium from peroxide damage.

Topical Formulations

In some embodiments of the disclosure described herein, the pharmaceutical composition is a topical formulation comprising an iodide ion and at least one carrier material. Non-limiting examples of carrier materials useful in the topical formulations disclosed herein are: thickeners, including gums, celluloses, acrylic acids, colloidal solids, hydrogels, and thermoreversible polymers; oil phases; surfactants, including non-ionic, anionic, and cationic; solvents, including polar and non-polar; preservatives, including antimicrobial, antioxidants and chelating agents; and pH adjustors, such as diethanolamine, lactic acid, monoethanolamine, triethanolamine, sodium hydroxide and sodium phosphate.

In various embodiments, the topical formulation is formulated for direct application to a body surface including but not limited to the skin or mucous membranes such as the vagina, anus, throat, eyes and ears. In some embodiments, the topical formulation is epicutaneous, i.e. directly applied to the skin. In various embodiments, the topical formulation is in the form of a cream, ointment, shake lotion, gel, powder, solid, transdermal patch, tincture, paste, vapor, tape, sponge or lotion.

Intravenous Formulations

In some embodiments of the disclosure described herein, the pharmaceutical composition is an intravenous formulation comprising an iodide ion and at least one carrier material. Non-limiting examples of carrier materials useful in the intravenous formulations disclosed herein are surfactants, including non-ionic, anionic, and cationic; solvents, including polar and non-polar; preservatives, including antimicrobial, antioxidants and chelating agents; and pH adjustors, such as diethanolamine, lactic acid, monoethanolamine, triethanolamine, sodium hydroxide and sodium phosphate.

Iontophoresis Delivery

In some embodiments of the disclosure described herein, the pharmaceutical composition is delivered through iontophoresis. In these embodiments, two electrodes are placed in contact with tissue, one of the electrodes being a pad of absorbent material soaked with a solution containing the iodide ion, and a voltage is applied between the electrodes to deliver the ion to the subject.

Sustained Release Formulations

In some embodiments of the disclosure described herein, the pharmaceutical composition is a sustained release formulation comprising an iodide ion and at least one carrier material. Non-limiting examples of carrier materials useful in the sustained release formulations disclosed herein are: enteric coatings, thickeners, including gums, celluloses, acrylic acids, colloidal solids, hydrogels, and thermoreversible polymers; oil phases; surfactants, including non-ionic, anionic, and cationic; solvents, including polar and nonpolar; preservatives, including antimicrobial, antioxidants and chelating agents; and pH adjustors, such as diethanolamine, lactic acid, monoethanolamine, triethanolamine, sodium hydroxide and sodium phosphate.

In various embodiments, the sustained release formulation is an ophthalmic formulation, a parenteral formulation, a pellet formulation, or a transdermal formulation.

In some embodiments, the sustained release ophthalmic formulation comprises a water-based gel, a suspension, an ointment, an ocular insert, or small colloidal carrier particles (such as liposomes, microspheres, microcapsules, nanoparticles, or nanocapsules). In some embodiments, the sustained release parenteral formulation comprises an oily vehicle, aqueous suspension, emulsion, microsphere, or an implantable drug delivery system. In some embodiments, the sustained release transdermal formulation comprises an iodide ion in an adhesive layer, a polymeric matrix layer, a reservoir layer or a peripheral adhesive layer.

Implants

In some embodiments of the disclosure described herein, the pharmaceutical composition is delivered through an implant comprising an iodide ion and at least one carrier material. In various embodiments, the implant is composed of a number of capsules. In some embodiments the implant is biodegradable.

Methods of Treatment

Disclosed herein, in certain embodiments, are methods of reducing or preventing oxidative stress processes in an individual in need thereof, comprising administering to the individual a composition comprising sodium iodide, catalase, or combinations thereof. In some embodiments, the method comprises administering a composition comprising between about 0.001% to about 10.0% sodium iodide by weight. In some embodiments, the method comprises administering a composition comprising between about 0.015% to about 5% sodium iodide by weight. In some embodiments, the composition has a basic pH. In some embodiments, the pH of the composition is between about 7.0 and about 8.4.

As discussed above, increased or undesired peroxide levels in a tissue (for example, ocular tissue) results from the inactivation (in a reversible reaction) of endogenous catalase by nitric oxide. The inactivation of catalase is associated with the destruction of nerve cells (glaucoma), retinal macular cells (AMD), lacrimal and epithelial cells (dry eye) and lens cells (cataract). In some embodiments, the methods described herein replace or supplement the function of inactivated catalase. In some embodiments, supplementation or replacement of catalase activity reduces or prevents oxidative stress processes.

In certain instances, peroxide inhibits or reduces the activity of enzymes needed for the proper functioning of a cell. In certain instances, these effects are reversible when the peroxide levels are lowered. In some embodiments, the methods described herein reverse the effects of undesired peroxide.

Photochemical Crosslinking

Disclosed herein, in certain embodiments, are methods of reducing or preventing oxidative stress processes in a tissue undergoing photochemical crosslinking, comprising administering to the tissue a composition comprising sodium iodide, catalase, or combinations thereof. In some embodiments, the method comprises administering a composition comprising between about 0.001% to about 10.0% sodium iodide by weight. In some embodiments, the method comprises administering a composition comprising between about 0.015% to about 5% sodium iodide by weight. In some embodiments, the composition has a basic pH. In some embodiments, the pH of the composition is between about 7.0 and about 8.4. In some embodiments, the tissue is a cornea. In some embodiments, the tissue is sclera.

In some embodiments, photochemical crosslinking further comprises removing the epithelium of the cornea and/or sclera, pretreating the cornea and/or sclera with chemicals (or utilizing other means to increase permeability of the surface of the cornea) before the tissue is irradiated. In some embodiments, pretreatment allows riboflavin and the iodide ions to readily penetrate into the stroma for crosslinking.

Diseases

Further disclosed herein, in certain embodiments, are methods of treating diseases, disorders or conditions associated with oxidative stress processes in an individual in need thereof, comprising administering to the individual a composition comprising sodium iodide, catalase, or combinations thereof. In some embodiments, the method comprises administering a composition comprising between about 0.001% to about 10.0% sodium iodide by weight. In some embodiments, the method comprises administering a composition comprising between about 0.015% to about 5% sodium iodide by weight. In some embodiments, the composition has a basic pH. In some embodiments, the pH of the composition is between about 7.0 and about 8.4.

Non-limiting examples of diseases and disorders for which the iodide-based solutions described here are useful include glaucoma, macular degeneration (wet and dry), cataract formation, keratoconus, cystoid macular edema, dry eye syndrome and quite a few more. In general, these conditions are described as oxidative ophthalmic disorders and the purpose of the pharmaceutical compositions described herein is to provide therapeutic relief to patients suffering from oxidative disorders by removal of peroxides. These applications are not specific to a particular anatomical part of the eye and in some embodiments are used to treat any ocular tissues that are exhibiting a pathogenesis of oxidative stress including but not limited to inflammation. In some embodiments, some of these conditions lead to irreversible vision loss and there are no current drugs or treatments available for some of these conditions.

In some embodiments the pharmaceutical compositions described herein is used to treat macular, retinal or scleral disorders. The compositions disclosed herein are introduced into an eye by any suitable methods. In these embodiments, the iodide ion is introduced by injection of iodide ion into the vitreous humor, using trans-scleral methods or implants of time released capsules or impregnated depot devices that slowly dissolve the iodide ion into the different chambers/parts of the eye.

In yet other embodiments, the pharmaceutical compositions described herein are used to treat other organ disorders, including the lungs, cardiovascular system and the brain. Amyloid beta formed in brain tissues inactivates catalase and the resulting hydrogen peroxide production is associated with Alzheimer's disease. Pharmaceutical compositions that allow an iodide ion to pass the blood-brain barrier are provided herein and are used in some embodiments to treat neurological disorders associated with oxidative stress.

Ectasia

Further disclosed herein, in certain embodiments, are methods of treating ectasia in a subject in need thereof, comprising administering to the subject a composition comprising sodium iodide, catalase, or combinations thereof. In some embodiments, the method comprises administering a composition comprising between about 0.001% to about 10.0% sodium iodide by weight. In some embodiments, the method comprises administering a composition comprising between about 0.015% to about 5% sodium iodide by weight. In some embodiments, the composition has a basic pH. In some embodiments, the pH of the composition is between about 7.0 and about 8.4.

In many post-operative surgical procedures negative side effects to the cornea and/or sclera are observed due to biological reactions termed "wound healing response". This wound healing response is the body's way of forming protective scar tissues when injury has been done.

In the cornea and/or sclera, the wound healing response is initiated by the surgical intervention. The primary means of orchestrating the wound healing response is by several cytokines that are released as result of the injury. These cytokines often use $H_2O_2$ as the secondary messenger molecules for stimulating the production of the new scar tissue, promoting edema, and changing the cellular functioning.

The corneal and scleral wound healing cycles are in at least some cases interrupted by adding an iodide ion or catalase into the eye before or shortly after the wound healing response begins. In some embodiments, iodide ion or catalase interrupts the corneal or scleral wound healing cycles. In some embodiments, dissociating $H_2O_2$ into water and molecular oxygen interrupts the corneal or scleral wound healing cycles. This interruption breaks the cascade of biological events that results in undesired side effects.

The cornea is particularly sensitive to oxidative stress. Hydrogen peroxide reacts with ambient UV and visible light in the blue spectrum to break apart into 2 $OH^-$ ions, which are the most destructive forms of ROS in the body.

The methods, compounds, and compositions described herein find use in the treatment of conditions characterized by oxidative stress or damage. As discussed infra, oxidative damage plays a role in the pathogenesis of many diseases. Non-limiting examples of diseases known to be associated with oxidative stress and therefore useful in the present disclosure are provided below.

Additional Ophthalmic Indications

In aspects of the disclosure, the methods and compositions described herein are beneficial in the treatment of ophthalmic conditions/diseases associated with oxidative stress. These conditions/diseases include, but are not limited to Glaucoma; Reduction of Inflammation; Dry Eyes; Degenerative Retinal Damage (ARMD); Cataractogenesis (process of cataract formation); Retinopathy of Prematurity (ROP); Ocular Uveitis; and Senile Cataracts.

Skin Indications

There are a number of skin conditions where the buildup of peroxide in the skin is of concern. For example, vitiligo affects nearly 2% of the world population and is one of the more difficult skin disorders to treat. It is known that vitiligo lesions contain very high levels of hydrogen peroxide and it has been suggested that hydrogen peroxide or nitric oxide buildup is the root cause of the disorder. The use of the pharmaceutical compositions described herein provide an improved method for decomposing hydrogen peroxide in the skin for vitiligo and other pigmentation disorders. In various embodiments the pharmaceutical composition introduces the iodide ion to the skin by topical administration, injection or iontophoresis.

Other skin disorders associated with hydrogen peroxide build up in the skin are androgenic alopecia (loss of hair) and the premature onset of gray hair. It has been demonstrated that superoxide anion and hydrogen peroxide build up is directly associated with both the onset of gray hair and androgenic alopecia. Provided herein, are compositions that treat gray hair or hair loss through the decomposition of hydrogen peroxide. In various embodiments, these compositions introduce an iodide ion to the skin by topical administration, injection, or iontophoresis.

In aspects of the disclosure, the methods and compositions described herein are useful in reversing, preventing or reducing detrimental skin conditions associated with oxidative stress. These conditions include, but are not limited to, premature aging, burns, Dermatitis; Psoriasis; Vitiligo, Androgenic Alopecia (loss of hair) and Onset of Gray Hair.

Joint Indications

In aspects of the disclosure, the methods and compositions described herein may be useful in reversing, treating or preventing joint conditions/diseases associated with oxidative stress. These conditions include, but are not limited to, Inflammation; Rheumatoid Arthritis; and Osteoarthritis.

Wound Healing Indications

In aspects of the disclosure, the methods and compositions described herein are useful in reversing, treating or preventing ocular wounds associated with oxidative stress. These conditions include, but are not limited to, pterygium, glaucoma, refractive corneal surgery such as PRK, LASIK, Intacs, lamellar corneal procedures, CK, and other thermokeratoplasty treatments and lens based refractive surgery, scleral surgery, retinal surgery or retinal or glaucoma laser surgery and intraocular such as cataract and eye lid surgery.

In some embodiments, the pharmaceutical composition is applied before or immediately after refractive surgeries in order to accelerate healing process. In other embodiments, the pharmaceutical composition is applied multiple times during the healing process. For example, following painful procedures, like PRK in which the epithelium is not healed, the pharmaceutical composition are applied periodically (weekly, daily or hourly) early in the postoperative period. In specific embodiments, a contact lens or bandage is impregnated with the iodide ion or catalase.

Heart Indications

In aspects of the disclosure, the methods and compositions described herein are useful in reversing, treating or preventing heart conditions/diseases associated with oxidative stress. These conditions include, but are not limited to, Angioplasty; Keshan Disease (Selenium Deficiency); Myocardial Infarction; Atherosclerosis (ASVD) and Arterial Sclerosis.

Lung Indications

In aspects of the disclosure, the methods and compositions described herein are useful in reversing, treating or preventing lung conditions/diseases associated with oxidative stress. These conditions include, but are not limited to, Asthma; Acute Respiratory Distress Syndrome (ARDS); Hyperoxia and Pulmonary Edema.

Local or Systemic Indications

In aspects of the disclosure, the methods and compositions described herein are useful in reversing, treating or preventing local and systemic conditions/diseases associated with oxidative stress. These conditions include, but are not limited to, Inflammatory Bowel Disease (IBD); Crohn's Disease; Ischemic Bowel Disease; Cancer; Inflammatory Immune Response; Diabetes; Injury Ischemia Reflow Injury; Vasospasm; Hemolytic Anemia; Progeria and Progressive Systemic Sclerosis.

Kidney & Liver Indications

In aspects of the disclosure, the methods and compositions described herein are useful in reversing, treating or preventing kidney and liver conditions/diseases associated with oxidative stress. These conditions include, but are not limited to, Hepatic Cirrhosis; Renal Graft; Glomerulonephritis and Endotoxin Liver Injury.

Neurological Indications

In aspects of the disclosure, the methods and compositions described herein are useful in reversing, treating or preventing neurological conditions/diseases associated with oxidative stress. These conditions include, but are not limited to, Parkinson's Disease; Alzheimer's Disease; Schizophrenia; Cerebral Edema; Cerebral Infarction (Stroke); Epilepsy; Bipolar Disorder; Trauma and Neurotoxins.

Aging-Related Indications

In aspects of the disclosure, the methods and compositions described herein are useful in reversing, treating or preventing diseases and symptoms associated with aging. These conditions include, but are not limited to, wrinkling, grey hair, baldness, presbyopia, cataracts, hearing loss, hypertension, and memory loss.

The above description of the disclosed embodiments is provided to enable any person skilled in the art to make or use the methods and compositions of the present disclosure. Various modifications to these embodiments will be readily apparent to those skilled in the art, and the generic principles described herein can be applied to other embodiments without departing from the spirit or scope of the disclosure. Thus, it is to be understood that the description and drawings presented herein represent a presently preferred embodiment of the disclosure and are therefore representative of the subject matter which is broadly contemplated by the present disclosure. It is further understood that the scope of the present disclosure fully encompasses other embodiments that may become obvious to those skilled in the art and that the scope of the present disclosure is accordingly not limited.

Examples

Corneal collagen cross-linking utilizing 0.5% riboflavin and 0.015% (1 mmol) sodium iodide was performed in over 200 eyes. Post-operative corneal haze, which results from keratocyte death due to the production of hydrogen peroxide and other harmful reactive oxygen species, was observed to be minimal, as compared to historical cross-linking procedures performed without sodium iodide, in which significant corneal haze has been observed to persist from 6 months to 1 year after the cross-linking procedure.

What is claimed:

1. A stable pharmaceutical composition for use in corneal collagen cross-linking, comprising (a) sodium iodide, (b) riboflavin, and (c) a pharmaceutically-acceptable excipient appropriate for ocular administration, wherein the pharmaceutical composition maintains a basic pH that permits iodide ion to catalytically break hydrogen peroxide into water and oxygen.

2. The pharmaceutical composition of claim 1, wherein the basic pH is between 7 and 8.4.

3. The pharmaceutical composition of claim 2, further comprising a reducing agent.

4. The pharmaceutical composition of claim 3, wherein the reducing agent is thiosulfate, vitamin C, or sodium bisulfate.

5. The pharmaceutical composition of claim 1, wherein the pharmaceutically-acceptable excipient is an artificial tear solution.

6. The pharmaceutical composition of claim 1, wherein the pharmaceutical composition is a solution adapted for introduction into the eye and diffusion into the cornea for promoting photochemical corneal cross-linking and reducing oxidative stress.

7. A method of treating a disease, disorder or condition characterized by unwanted or excessive oxidative stress in an individual in need thereof, comprising administering to the individual the pharmaceutical composition of claim 1.

8. The method of claim 7, wherein the disease, disorder or condition is Glaucoma; Dry Eyes; Degenerative Retinal Damage (ARMD); Cataractogenesis; Retinopathy of Prematurity (ROP); Ocular Uveitis; Presbyopia; or Cataracts.

9. A method for photochemical crosslinking comprising administering the pharmaceutical composition of claim 1 to a tissue in need thereof.

10. The method of claim 9, wherein the pharmaceutical composition comprises between about 0.001% to about 10.0% sodium iodide by weight.

11. The method of claim 9, wherein the pharmaceutical composition comprises between about 0.015% to about 5% sodium iodide by weight.

12. The method of claim 10, wherein the pharmaceutical composition comprises about 0.015% sodium iodide by weight and about 0.5% riboflavin by weight.

13. The method of claim 9, wherein the basic pH is between 7 and 8.4.

14. The method of claim 9, wherein the pharmaceutical composition further comprises a reducing agent.

15. The method of claim 14, wherein the reducing agent comprises thiosulfate, vitamin C, or sodium bisulfate.

16. The method of claim 9, wherein the pharmaceutical composition is used to treat wounds associated with refractive corneal surgery, thermokeratoplasty treatment, lens-based refractive surgery, retinal surgery, scleral surgery, retinal or glaucoma laser surgery, cataract and eye lid surgery, PRK, LASIK, Intacs, lamellar corneal procedures, CK, or any combinations thereof.

17. A method of reducing oxidative stress in a tissue undergoing photochemical crosslinking, comprising contacting the tissue with the pharmaceutical composition of claim 1.

18. The method of claim 17, wherein the pharmaceutical composition comprises between about 0.015% to about 5% sodium iodide by weight.

19. The method of claim 17, wherein the composition has a basic pH between 7 and 8.4.

* * * * *

UNITED STATES PATENT AND TRADEMARK OFFICE
CERTIFICATE OF CORRECTION

| | | |
|---|---|---|
| PATENT NO. | : 10,092,594 B2 | Page 1 of 1 |
| APPLICATION NO. | : 15/335146 | |
| DATED | : October 9, 2018 | |
| INVENTOR(S) | : Roy S. Rubinfeld, Raymond A. Hartman and Sandy T. Feldman | |

It is certified that error appears in the above-identified patent and that said Letters Patent is hereby corrected as shown below:

On the Title Page

Item (71) should read Applicants: CXL Ophthalmics, LLC, Encinitas, CA (US). Please remove "Brad Hartman, Renton, WA (US)"

Signed and Sealed this
Thirtieth Day of July, 2019

Andrei Iancu
*Director of the United States Patent and Trademark Office*